US009383420B2

(12) United States Patent
Virtanen et al.

(10) Patent No.: US 9,383,420 B2
(45) Date of Patent: Jul. 5, 2016

(54) LOW-FIELD NMR DEVICE FOR MEASURING THE WATER CONTENT OF SOLIDS AND SLURRIES

(75) Inventors: Sami Virtanen, Espoo (FI); Veli-Pekka Viitanen, Huhmari (FI)

(73) Assignee: METSO AUTOMATION INC., Vantaa (FI)

( * ) Notice: Subject to any disclaimer, the term of this patent is extended or adjusted under 35 U.S.C. 154(b) by 687 days.

(21) Appl. No.: 13/818,712

(22) PCT Filed: Aug. 30, 2011

(86) PCT No.: PCT/FI2011/050753
§ 371 (c)(1), (2), (4) Date: Feb. 25, 2013

(87) PCT Pub. No.: WO2012/028785
PCT Pub. Date: Mar. 8, 2012

(65) Prior Publication Data
US 2013/0154644 A1 Jun. 20, 2013

(30) Foreign Application Priority Data
Aug. 31, 2010 (FI) .................................... 20105917

(51) Int. Cl.
*G01R 33/28* (2006.01)
*G01R 33/44* (2006.01)
(Continued)

(52) U.S. Cl.
CPC ................ *G01R 33/28* (2013.01); *G01N 24/08* (2013.01); *G01N 24/081* (2013.01); (Continued)

(58) Field of Classification Search
CPC ... G01N 24/08; G01N 24/081; G01N 24/082; G01N 24/085; G01R 33/28; G01R 33/381; G01R 33/44; G01R 33/445
USPC ................................................ 324/300–322
See application file for complete search history.

(56) References Cited

U.S. PATENT DOCUMENTS 6,242,912 B1 * 6/2001 Prammer ............. G01N 24/081 324/303
2005/0030020 A1 * 2/2005 Siess ....................... G01V 3/32 324/303

(Continued)

FOREIGN PATENT DOCUMENTS

EP 1 006 366 A1 6/2000
WO WO 01/14847 A2 3/2001
WO WO 03/006974 A1 1/2003

OTHER PUBLICATIONS

Mar. 11, 2015 Office Action issued in Chinese Application No. 201180052744.2

(Continued)

*Primary Examiner* — Melissa Koval
*Assistant Examiner* — Rishi Patel
(74) *Attorney, Agent, or Firm* — Oliff PLC

(57) ABSTRACT

A Nuclear Magnetic Resonance (NMR) apparatus and method for measuring the water content of samples has a device to produce a main magnetic field; a sample receiving space within a main magnetic field; a device to excite a measurable RF magnetization to a sample placed into the sample receiving space at an operating frequency defined by the main magnetic field; a device to measure the RF signal produced by the excited sample; and a device to determine the water content in the sample based on the RF signal. The sample receiving space is capable of accommodating a sample having a volume of at least 0.5 $dm^3$, and the device to produce a main magnetic field has a resistive electromagnet which is adapted to produce a main magnetic field corresponding to an operating frequency of 400-2000 kHz.

13 Claims, 4 Drawing Sheets

(51) Int. Cl.
*G01N 24/08* (2006.01)
*G01R 33/381* (2006.01)

(52) U.S. Cl.
CPC .......... *G01N 24/082* (2013.01); *G01N 24/085* (2013.01); *G01R 33/381* (2013.01); *G01R 33/44* (2013.01); *G01R 33/445* (2013.01)

(56) References Cited

U.S. PATENT DOCUMENTS

| | | | | |
|---|---|---|---|---|
| 2006/0112628 | A1 | 6/2006 | Kotyk et al. | |
| 2009/0140736 | A1 | 6/2009 | Ogawa et al. | |
| 2010/0304976 | A1* | 12/2010 | Overweg ............. | G01R 33/381 505/162 |
| 2012/0249134 | A1* | 10/2012 | Rapoport ........... | G01R 33/3804 324/307 |

OTHER PUBLICATIONS

Wang Weimin et al., "The Fundamental Study on NMR Logging", WLT, 1997, vol. 21, No. 6, pp. 385-392.

Supplementary European Search Report issued in European Application No. EP 11 82 1175 issued May 21, 2014.

Hutchison et al., "A Whole-Body NMR Imaging Machine," *Journal of Physics E. Scientific Instruments*, Institute of Physics, Bristol, Great Britain, Sep. 1, 1980, vol. 13, No. 9, pp. 947-955.

Hills et al., "Motional Relativity and Industrial NMR Sensors," *Journal of Magnetic Resonance*, Academic Press, Orlando, Florida, Feb. 1, 2006, vol. 178, No. 2, pp. 193-205.

Lewis et al., "Use of NMR for Measurement of Total Body Water and Estimation of Body Fat," *Journal of Applied Physiology*, Mar. 1986, vol. 60, No. 2, pp. 836-840.

Brosio et al., "Moisture Determination in Starch-Rich Food Products by Pulsed Nuclear Magnetic Resonance," *International Journal of Food Science and Technology*, Apr. 1, 1978, vol. 13, No. 2, pp. 107-116.

Cutmore et al., "Determination of Moisture in Black Coal Using Pulsed Nuclear Magnetic Resonance Spectrometry," *Fuel*, IPC Science and Technology Press, Guildford, Great Britain, Jan. 1, 1986, vol. 65, No. 1, pp. 34-39.

Callaghan et al., "Earth's Field NMR in Antarctica: A Pulsed Gradient Spin Echo NMR Study of Restricted Diffusion in Sea Ice," *Journal of Magnetic Resonance*, Academic Press, Orlando, Florida, Jul. 1, 1998, vol. 133, No. 1, pp. 148-154.

Redpath, "Signal-to-Noise Ratio in MRI," *The British Journal of Radiology*, Jul. 1998, vol. 71, pp. 704-707.

Barale et al., "The Use of a Permanent Magnet for Water Content Measurements of Wood Chips," *IEEE Transactions on Applied Superconductivity*, Mar. 2002, vol. 12, No. 1, pp. 975-978.

Butler et al., "Using Low-Field MRI to Improve Tablet Dissolution Testing," *Tablets & Capsules*, Jan. 2010.

Kantzas et al., "Low Field NMR Applications in Oil Sands Mining and Extraction," International Symposium of the Society of Core Analysts, Toronto, Canada, Aug. 21-25, 2005.

Ruan, "Water in Foods and Biological Materials," *P.L. Chem.*, Food Control, vol. 10, 1999, Book Review.

Schmidt et al., "Quantitative Determination of Water in Speciation in Aluminosilicate Glasses: A Comparative NMR and IR Spectroscopic Study," *Chemical Geology*, 2001, vol. 174, pp. 195-208.

Belton et al., "Pulsed NMR Studies of Water Striated Muscle," *Biochimica et Biophysica Acta*, 1974, vol. 354, pp. 305-314.

Office of Industrial Technologies, "Sensors & Controls Project Fact Sheet," Energy Efficiency and Renewable Energy, U.S. Department of Energy.

International Search Report issued in International Patent Application No. PCT/FI2011/050753 dated Jan. 27, 2012.

International Preliminary Report on Patentability issued in International Patent Application No. PCT/FI2011/050753 dated Sep. 28, 2012.

Sensors and Controls Project Fact Sheet, "Remote Automatic Material On-Line Sensor", Office of Industrial Technologies, Energy Efficiency and Renewable Energy, U.S. Department of Energy, May 2000, pp. 1-2.

* cited by examiner

LOW-FIELD NMR DEVICE FOR MEASURING THE WATER CONTENT OF SOLIDS AND SLURRIES

FIELD OF THE INVENTION

The invention relates to Nuclear Magnetic Resonance (NMR) measurement devices and methods. In particular, the invention relates to a NMR device and method for measuring water content of solids and slurries.

BACKGROUND OF THE INVENTION

NMR measurements are based on providing a net magnetization to a large group of atomic nuclei using a static magnetic field (main field) and deflecting the net magnetization from the direction of the static magnetic field using a radio frequency pulse (RF pulse) of a radio frequency magnetic field (RF field), the operating frequency (Larmor frequency) being defined by the nuclei concerned and the magnitude of the main field. The relaxation of the deflected precessing net magnetization can be detected by measuring the NMR signal, i.e. the EMF induced in the receiving RF coils caused by the precessing net magnetization, which is gradually relaxing back to parallel with the main field (known also as Free Induction Decay, FID)). The relaxation speed is determined by the homogeneity of the main field and the properties of the matter under measurement.

Water content of various material samples can be measured accurately and rapidly using NMR spectroscopy or relaxometry. Wide usage of NMR based moisture content measurement devices has been hindered mainly by the high cost of measurement devices. In particular, in many applications, e.g. biomass water content measurements, the desired sample volume is of the order of several deciliters or larger, which sets practical limits for device dimensions and other specifications.

Prior art [e.g. Remote Automatic On-Line Sensor; Final Report. Quantum magnetics Inc] suggests that a minimum operating frequency of 5 to 6 MHz should be used in NMR-based water content measurements in order to maintain a reasonable recovery time, i.e. receive circuit deadtime following the transmitted RF pulse. This necessitates the use of a relatively high main magnetic fields (>125 mT). High field also increases the measurable signal amplitude. Other prior art [The British Journal of Radiology, 71 (1998), 704-707] also teaches that the electromotive force induced in the receiving coils by the NMR signal is essentially proportional to the square of the main magnetic field strength. However, the use of field strengths of this magnitude increases device costs, power consumption and magnet mass, for example. In addition, the temperature variation and main field inhomogeneity effects are significant in high fields, further complicating device design. Also safety aspects, as concerns e.g. a stray magnetic field outside the device, become more relevant in high magnetic fields. The above aspects are emphasized if the desired sample volume is large. Barak, P. J. et al, "*The Use of a Permanent Magnet for Water Content Measurements of Wood Chips*", IEEE TRANSACTIONS ON APPLIED SUPERCONDUCTIVITY, VOL. 12, NO. 1, March 2002, present that the water content of wood chips can be measured at a 0.47 T main field, yielding for the operating frequency 20 MHz. The permanent magnet used weighed 68 kg although the possible sample volume ("good field" volume) was only less than 10 ml. Other examples of prior art include water content analysis in dissolution testing, for example as presented by Butler James et al, "*Using low-field MRI to improve*

*tablet dissolution testing*", Tablets & Capsules, January 2010 at 0.5 T main field and small sample volume.

There have also been attempts to use lower frequencies and field strengths. For example, Kantzas A. et al, "*LOW FIELD NMR APPLICATIONS IN OIL SANDS MINING AND EXTRACTION*", International Symposium of the Society of Core Analysts, Toronto, Canada, 21-25 Aug. 2005, have used a 1 MHz Corespec 1000™ (main field 24 mT produced by permanent magnet) relaxometer apparatus to determine the oil and water content in 20 ml ore and froth samples.

It is relatively easy to produce the required field strength with a good homogeneity over small sample volumes with permanent magnets, as in the prior art referred to above. Large sample volumes are, however, required in many applications, because of sampling standards, as well as the generally large particle dimensions e.g. of biomass samples. The device designs referred to above are, however, not suitable for measuring large sample volumes since the device designs would turn out to be expensive and difficult to manufacture if scaled up to the required size.

SUMMARY OF THE INVENTION

It is an object of the invention to provide a novel NMR-based water content measurement apparatus and method suitable for the measurement of large sample volumes (0.5 l or more). In particular, it is an aim to provide an apparatus. A further aim is to provide an apparatus which can be designed to be lightweight.

The invention is based on the idea of utilizing a measurement volume of at least 0.5 liters and a low operating frequency of 400-2000 kHz, which have, according to the invention, found to be achievable using a resistive electromagnet. More specifically, the invention is defined in the independent claims.

According to one embodiment, the apparatus comprises

- a sample receiving space capable of accommodating a sample having a volume of at least 0.5 $dm^3$,
- a resistive electromagnet for producing a main magnetic field over the entire sample receiving space at a field strength of 10-40 mT,
- an RF coil for exciting a measurable precessing transverse magnetization to a sample placed into said sample receiving space at a Larmor frequency defined by said main magnetic field,
- means for measuring the RF signal produced by the excited sample, preferably using the same RF coil which is used for excitation, and
- a computing unit for determining the water content in the sample based on the RF signal.

The method comprises

- resistively producing a main magnetic field over a sample having a volume of at least 0.5 $dm^3$,
- subjecting the sample to said main magnetic field in order to produce a net magnetization to the sample,
- exciting a measurable RF magnetization to a sample at an operating frequency of 400-2000 kHz,
- measuring the RF signal produced by the excited sample, and
- determining the water content in the sample based on the RF signal.

The sample can be a biomass sample typically in a solid or slurry form.

According to one embodiment, a passively cooled electromagnet is used for producing the main magnetic field, the operating frequency preferably being 400-950 kHz in order for the amount of heat produced being sufficiently low.

According to one embodiment, an actively cooled electromagnet is used, whereby the operating frequency can be as high as 950-2000 kHz.

According to one embodiment the mass of the sample is measured while the sample is in the sample receiving space and the relative water content of the sample is determined partly based on the mass of the sample.

According to one embodiment, the RF signal is measured only after a predetermined dead time after the excitation pulse in order for the measurement electronics to recover from the excitation pulse. The assumed RF signal value at the time of the excitation pulse is estimated based on the measured RF signal by extrapolation and said estimated RF signal value is used in determining the water content of the sample. By using such measurement sequence and signal processing algorithm the utilization of such large measurement volume and low magnetic field (low Larmor frequency) can be used, contrary to the expectations of prior art. It is an advantage of the invention that the ability to measure also tight bound water in dry biomass samples is not compromised. As concerns this problem, we refer to "*Water in Foods and Biological Materials*", R. R. Ruan, P. L. Chen, CRC Press 1998.

Typically, the dead time referred to above is 30-200 μs.

The preferred operation frequency of the apparatus is 400-1700 kHz.

The invention provides significant advantages. First, the device can be designed to be small and cost-effective compared with NMR devices based on permanent magnets or superconducting magnets. Second, it extends the measurement volume of small-scale devices to the deciliter range while maintaining the ability to determine the water content in the sample. Thus, for example the water content of biomasses and biofuels can be measured conveniently.

Is should be noted that in the case of small sample volumes, the temperature of the main coil is not a limiting factor as the resistance of the coil is typically low and thus also the power dissipation of the coil is at low level. However, it has been found that with volumes over 0.5 $dm^3$, the present operating range is desired as the temperature of the coil remains at an acceptable level.

Additional advantages obtained by means of the ability to use low main magnetic field and thus low frequency are

- low power consumption,
- low magnet temperature,
- low magnet mass,
- no or low temperature dependence of magnetic field,
- ability to use an electromagnet for producing a homogeneous magnetic field without any shimming coils,
- safe level of stray field,
- more slack relative uniformity requirement for the magnetic field,
- lower cost of amplifiers, AD-converters, power supplies etc.

In summary, a more cost-effective, lightweight and safe-to-use device can be manufactured.

According to a preferred embodiment, the measurement system comprises integral sample mass measuring means. Preferably, the weight of the sample can be measured while the sample is in the sample receiving space of the NMR device, i.e. in the NMR signal measurement position. The sample weight measured is utilized together with the extrapolated NMR signal in determination of the water content of the sample.

The term "sample receiving space" means, in particular, a zone within the main magnetic field having a field strength of 10-40 mT and field homogeneity better than 1000 ppm, preferably better than 250 ppm. Typically there are provided holding means in the main magnet for holding a sample vessel such that the sample is located within the sample receiving space. Depending on the shape of the main coil, the sample receiving space can have various shapes.

The term "resistive electromagnet" refers to a coil typically wound from a metal conductor which is in resistive state, in contrast to superconducting state, at the operating temperature of the apparatus (typically room temperature).

Further advantages and embodiments of the invention are discussed in the following detailed description with reference to the attached drawings.

DETAILED DESCRIPTION OF EMBODIMENTS

Figure 1:
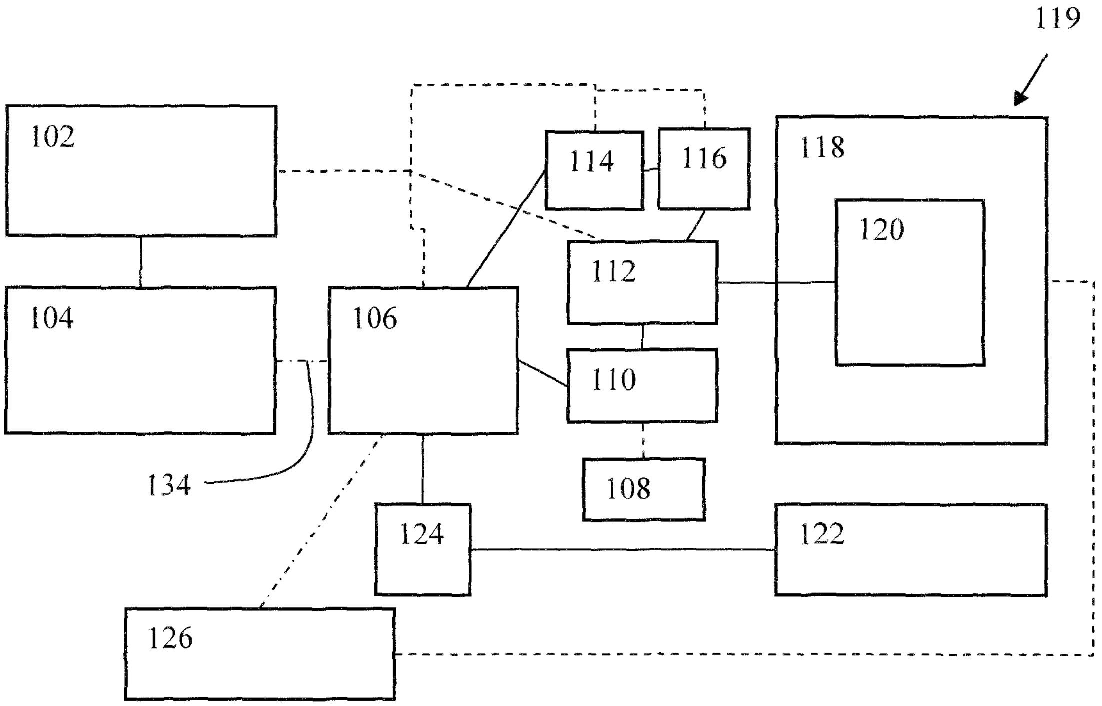
FIG. 1 shows a measurement system according to one embodiment of the invention.

A measurement system according to one embodiment is shown in FIG. 1. The NMR unit is denoted with the reference numeral 119 and comprises a main DC electromagnet 118 and an RF coil 120 placed inside the main magnet 118. The main magnet 120 is powered by a DC power supply 126. The system also comprises a control and data acquisition computer 102. The computer 102 is connected via a control signal and data transmission channel 134 to an ADC and DAC converter 106. The RF coil 120 is connected to a directional switch 112 which is used for transmitting both the excitation signal from the ADC/DAC 106 to the RF coil 120 and the NMR signal from the RF coil 120 to the ADC/DAC 106. The excitation signal 132 is transmitted through an RF power amplifier 110 powered by a suitable power supply 108. and the NMR signal is received via input amplifiers and low pass filters 114, 116 The weight of the sample placed inside the RF coil is measured using a load cell 122 connected via a load cell amplifier 124 to the ADC/DAC 106. Power for the separate units of the system is provided using a general power supply 102 or, as discussed above, using separate power supplies such as usually required by the main magnet and the RF amplifier 110. Power lines are drawn an dashed lines in FIG. 1, whereas the control/data lines are drawn as dash/dot lines. The RF transmit/receive signal lines and the mass weight signal lines are drawn as solid lines.

As discussed above, the main magnet 118 is adapted to produce a magnetic field corresponding to a Larmor frequency of 400-2000 kHz of protons in the sample. In practice, the field strength should be about 9-44 mT at the sample receiving zone within the RF coil 120. The main magnet is preferably an electromagnet with a winding scheme adapted to produce as homogeneous field at the sample receiving zone as possible. According to one embodiment, the main magnet 118 is wound from aluminum conductor.

The main magnet is preferably a resistive electromagnet which is passively or actively cooled. Passive cooling in this context means that heat is dissipated from the main magnet only through natural radiation, convection and conduction from the magnet material to its surroundings. Active cooling may take place in the form of forced fluid circulation, such as forced air circulation.

The NMR signal frequency is directly proportional to the main magnetic field, the proportionality coefficient being the gyromagnetic ratio. On the other hand, the magnetic field of an electromagnet is directly proportional to the electrical current flowing in the magnet coil. Further, the electrical power required to drive the current is proportional to the coil resistance multiplied by the square of the current. In practice, the coil resistance increases almost linearly with the coil temperature, which in turn increases with the increasing current; thus the power consumption of the coil is practically a steeper function of the current than the square of the current.

The RF coil 120 is adapted to produce a magnetic field perpendicular to the main magnetic field. The RF coil 120 can be of a birdcage type. The size of the RF coil 120 is sufficient to accommodate a sample having a volume of at least 0.5 $dm^3$, preferably 0.5-5 $dm^3$. In particular, the sample receiving zone inside the RF coil can be shaped to be cylindrical, but other shapes are possible too.

The sample weighing device 122 can be placed inside or outside the NMR unit 119. Preferably, it is placed below the NMR unit 119 and the dead load of the NMR unit is taken into account by suitable calibration or computationally.

Figure 2A:
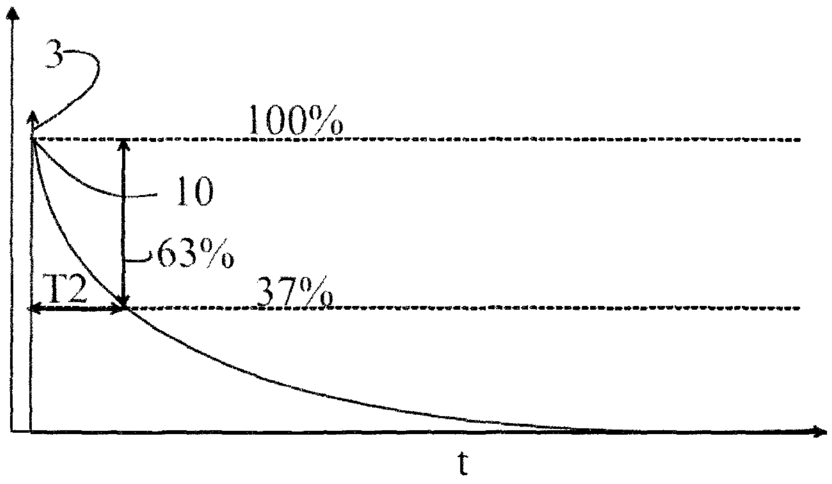
FIG. 2*a* presents graphically typical NMR signals with their relaxation times.

In a humidity measurement, a homogeneous DC magnetic field is generated by the main magnet into the sample to be measured, then interaction of the magnetic field with the hydrogen in the sample causes a small magnetization to develop in the sample. Next, with reference to FIGS. 2 and 3, the sample is exposed to a short intense radio frequency (RF) excitation pulse 3 by the RF coil, which excites the hydrogen nuclei. In the following step the NMR signal is recorded by the RF coil, typically for a period of milliseconds. During this time, the sample undergoes NMR relaxation and returns to the original magnetization state. The signal amplitude 10 (FIG. 2) is proportional to the total amount of hydrogen from moisture of the samples. However, for practical reasons, the recordation cannot be started immediately after the excitation pulse 3, but only after a predetermined dead time (of the order of tens of microseconds following the first RF pulse, typically 50-200 microseconds). However, it is the maximum value of the NMR signal that defines the moisture content, whereby this maximum value 10 is extrapolated from the NMR signal recorded after the dead time. The NMR signal arising from the protons of the solid matter in the sample decays in <50 microseconds, and thus advantageously does not affect the definition of moisture in the sample, as described above.

In summary, according to a preferred embodiment, the NMR signal is measured after a predefined period of dead time after the excitation pulse and an algorithm is used that utilizes the signal data measured after said dead time and extrapolates the signal to zero time (at the time of the excitation pulse). On the basis of the extrapolated signal, the water content of the sample is determined. Extrapolation methods known per se can be used.

The decay of the signal as illustrated in FIG. 2 is determined mostly by the T2, i.e. the spin-spin relaxation time, of the sample.

The present NMR device is especially well suited for measuring the water content in biomass. When the sample to be measured is very dry, typically meaning water content of less than 20 m-%, the signal-to-noise-ratio is low, which can be compensated for by increasing the number of successive measurements and averaging them. This easily leads to a long measurement time. The limitation for the time between successive measurements is primarily set by time factor T1, i.e. the spin-lattice relaxation time. This is the time required for the deflected average magnetization vector to recover its original value. The recovery is enabled by energy dissipation from the protons to the lattice. If the excitation pulse is applied before full relaxation, reduced signal amplitude is observed, and the correlation coefficient between the water content and the signal amplitude is altered, and thus calibration will not be valid.

Low magnetic field and low Larmor frequency enable the construction of a large sample volume measurement system that has much lower mass, power consumption and cost than what can be expected based on the prior art.

According to one embodiment, the RF signal is measured only after a predetermined dead time after the excitation pulse in order for the measurement electronics to recover from the excitation pulse. For obtaining the most accurate estimate for the water content, the assumed RF signal value at the time of the excitation pulse is extrapolated based on the measured RF signal. This can be done following the principles illustrated in FIGS. 2*a* and 2*b*.

Figure 2B:
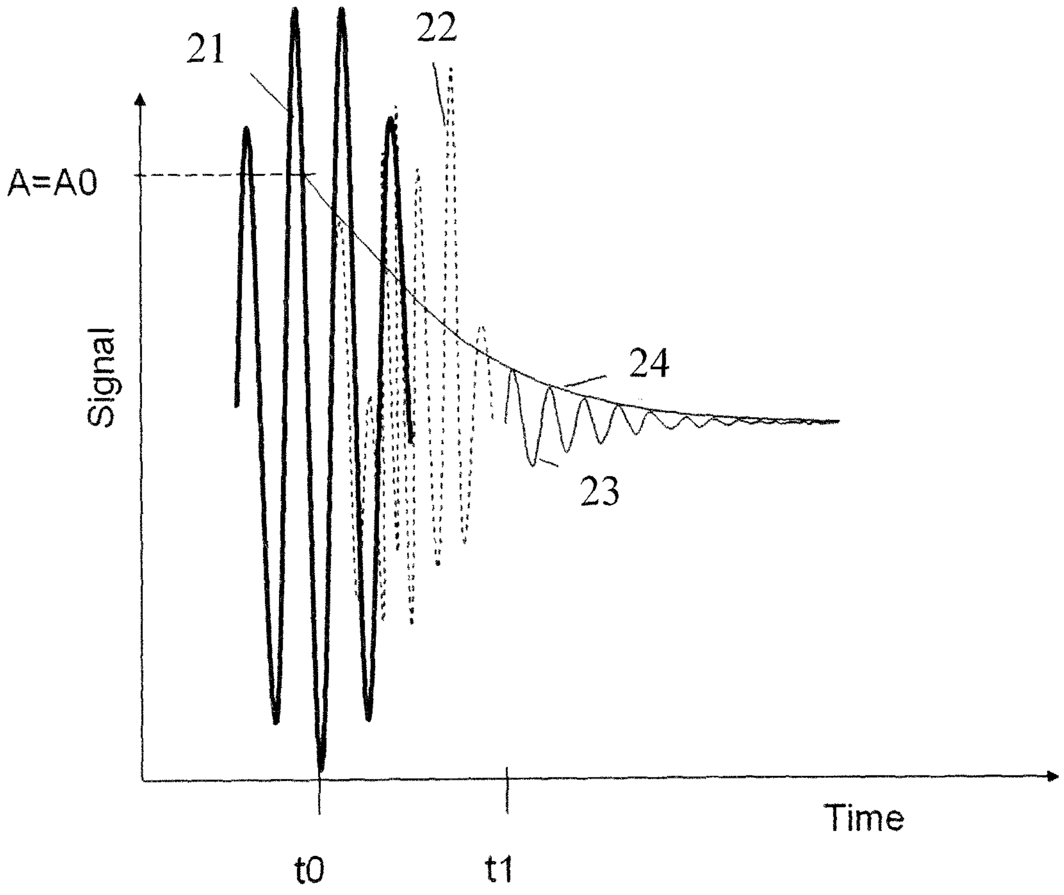
FIG. 2*b* illustrates as a graph extrapolation of NMR signal according to one embodiment of the invention.
Figure 3:
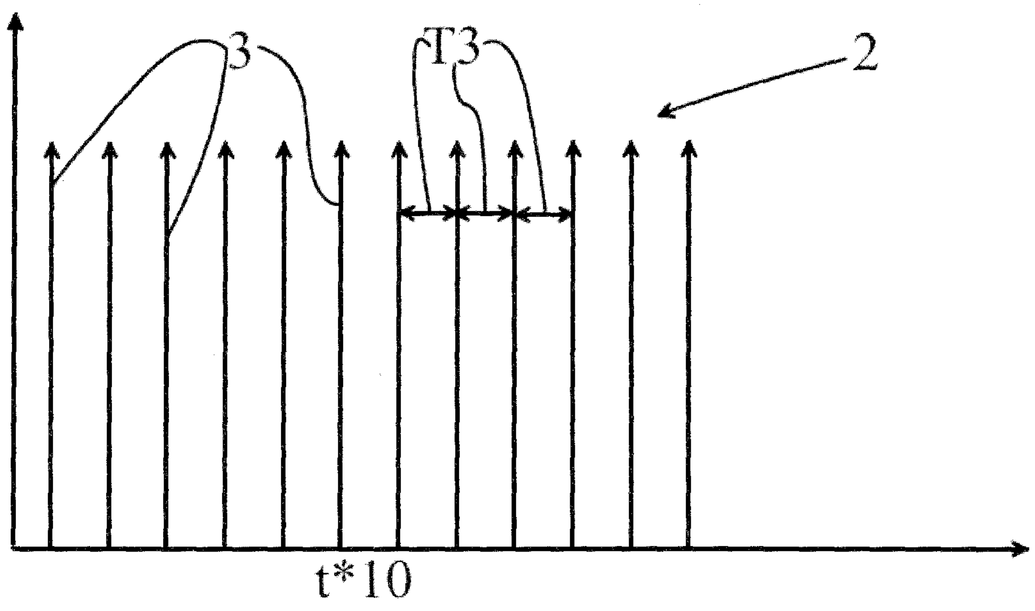
FIG. 3 presents a typical pulse sequence in accordance with the invention.
Figure 4:
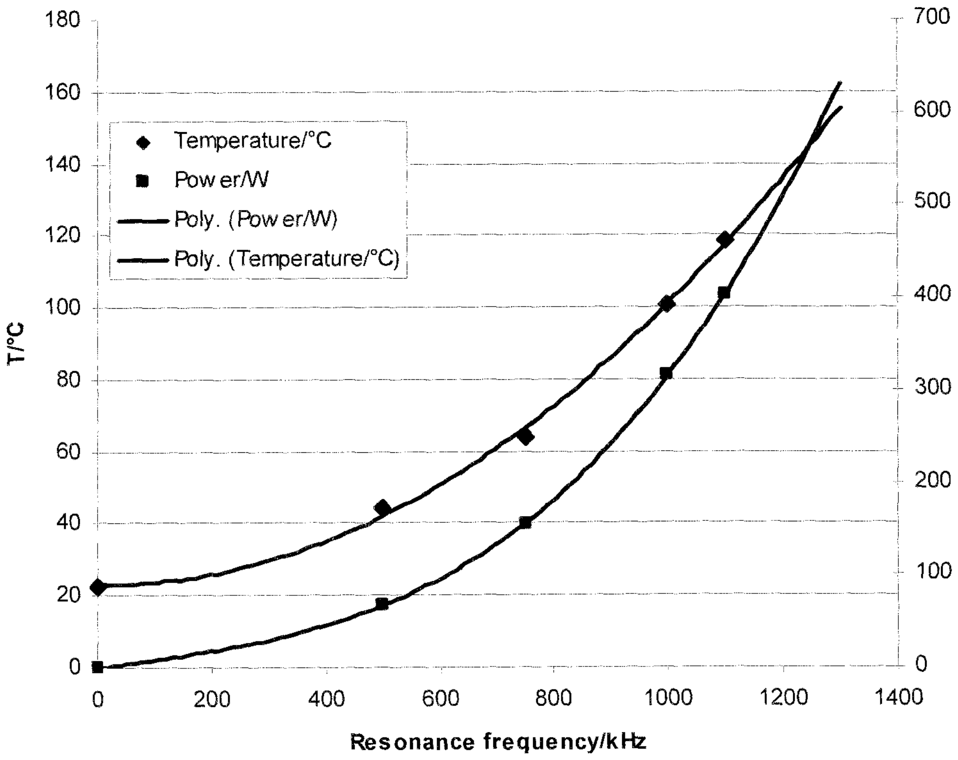
FIG. 4 shows a temperature/power vs. resonance frequency curve of aluminum coil electromagnet.

Referring to FIG. 2*b*, free induction decay signal amplitude 23 is very small compared to the original 90 degree excitation pulse 21. In order to record data without serious interference, it is necessary to wait until the excitation pulse as well as the noise and ringing 22 it has induced in the measurement electronics is attenuated to a harmless level, or otherwise utilize only data recorded after t=t1.

Free-induction decay signal attenuation can advantageously be described by an exponential $$S = A0 \cdot e^{-\frac{t}{T2}}$$

or Gaussian function $$S = A0 \cdot e^{-\left[\frac{t}{T2}\right]^2}$$

Assuming that t1−t0>50 microseconds, which is generally true for NMR devices operating below 2 MHz Larmor frequencies, the signal arising from solids is not detectable and the water content of the sample is proportional to extrapolated amplitude A0 at t=t0. Since the spin-spin relaxation time T2 is strongly dependent on the material and its water content, one cannot directly use the amplitude value at t=t1 to determine the water content.

In order to find out the value of A0, it is necessary to mathematically extrapolate the envelope 24 of the signal amplitude recorded at t>t1 backwards to t0, advantageously by fitting the abovementioned functions to the data at t>t1.

It should be noted that such problem relating to long dead time does not occur if the sample volume is small, especially if combined with a high Larmor frequency as in the prior art. This is because the RF power needed for exciting a small sample is low and the excitation pulse, including unwanted transients and ringing, can be short, whereby the dead time of the receiver is also very short. Also the inductance of the RF coil can be kept low with small samples even if its gain were high, which aids in minimizing the dead time of the circuitry. However, in the case of large sample volumes, the dead time inevitably becomes a significant factor, which can be taken into account using the algorithm shortly described above. The dead time can naturally be shortened by significantly reducing the Q-value of the RF-coils, but this would degrade the signal-to-noise ratio below acceptable levels.

It has been found by the inventors that the upper limit of the present frequency range arises from the thermal limitations of a passively cooled or air-cooled electromagnet. For a passively cooled magnet with 6 kg of aluminum conductor, a magnetic field exceeding 18 mT corresponding to Larmor frequency exceeding 950 kHz leads to magnet surface temperatures that are above the acceptable values both for the sample as well as for the user. Table 1 below lists ergonomics data to establish temperature limit values for hot surfaces according to the guideline EN 563. Forced air cooling may increase the usable magnetic field/frequency range up to about 35 mT/1700-2000 kHz.

TABLE 1

EN 563: 1994 Safety of machinery - Temperatures of touchable surfaces - Ergonomics data to establish temperature limit values for hot surfaces

| Materials/time-temp* | 1 sec | 4 sec | 10 sec | 10 min | 8 hr |
|---|---|---|---|---|---|
| uncoated metal | 65 | 58 | 55 | 48 | 43 |
| painted metal | 83 | 64 | 55 | 48 | 43 |
| enamelled metals | 74 | 60 | 56 | 48 | 43 |
| ceramics, glass, stone | 80 | 70 | 66 | 48 | 43 |
| plastics | 85 | 74 | 70 | 48 | 43 |
| wood | 110 | 93 | 89 | 48 | 43 |

It should also be noted that the temperature aspect is not relevant for small sample volume devices, because permanent magnets can be used or the required current densities in the main coil are significantly lower, resulting in low heat dissipation.

The lower frequency limit, on the other hand is set by two different phenomena. First, the detected signal amplitude is approximately proportional to the square of the magnetic field strength. Thus, the S/N-ratio decreases rapidly when the Larmor frequency decreases. S/N-ratio is a significant problem when measuring the water content of dry samples with a low magnetic field producing a low Larmor frequency, as is the case in the invention. Secondly, the dead time after excitation is basically inversely proportional to the Larmor frequency. When the frequency drops to one half, the time required for the electronics and the RF-coil to recover from the excitation pulse doubles (basically same number of attenuation cycles), and exceeds manyfold the spin-lattice relaxation time constant of samples with tightly bound water, thus limiting the measurement range to wet fuels. The dead time problem is aggravated by the large sample volume needed, which leads to large inductance of the excitation/receiving coils and thus slow recovery. Below the present lower frequency limit of 400 kHz, the dead time is too long for practical purposes, and the accuracy of the signal extrapolation and thus the accuracy of the measurement is compromised.

Integrating a weighing device into the system is preferred so as to be able to express the moisture content as the ratio of water mass and total mass. Typically in the prior art, this has been achieved by measuring also the NMR signal emanating from the solids in the sample. This is a less accurate method, and furthermore impossible to realize with the low frequencies used in this invention.

The invention claimed is:

1. A Nuclear Magnetic Resonance (NMR) apparatus for measuring the water content of samples of solids and/or slurries, comprising:

means for producing a homogeneous main magnetic field, a sample receiving space within said main magnetic field, means for producing a magnetic RF pulse for exciting a measurable RF magnetization to a sample placed into said sample receiving space at an operating frequency corresponding to the Larmor frequency of hydrogen nuclei in the sample, the operating frequency being directly proportional to said main magnetic field, the means for producing a magnetic RF pulse being inside the means for producing a homogeneous main magnetic field, and the RF magnetic field being perpendicular to the main magnetic field, means for measuring the RF signal of a free induction decay produced by the excited sample, and means for determining water content in the sample on the basis of said measured RF signal, wherein the means for measuring the RF signal being configured to measure the RF signal of the excited sample after a predetermined dead time after the excitation pulse, said means for determining the water content of the sample are adapted to extrapolate the RF signal value to the time at the excitation pulse based on the measured RF signal and adapted to utilize said extrapolated signal value in determining the water content of the sample, the sample receiving space is capable of accommodating a sample having a volume of at least 0.5 $dm^3$ inside the means for producing a magnetic RF pulse, and the means for producing a main magnetic field comprise a cooled resistive electromagnet wound with an aluminum conductor which is adapted to produce a main magnetic field corresponding to an operating frequency of 400-2000 kHz of the free induction decay.

2. The apparatus according to claim 1, wherein the electromagnet is passively cooled.

3. The apparatus according to claim 1, wherein by further comprising means for actively cooling the electromagnet, by forced air circulation.

4. The apparatus according to claim 1, wherein the winding scheme is adapted to produce the main magnetic field corresponding to the operating frequency of the device is 400-950 kHz.

5. The apparatus according to claim 1, wherein the winding scheme is adapted to produce the main magnetic field corresponding to the operating frequency of the device is 950-2000 kHz.

6. The apparatus according to claim 1, wherein by further comprising means for measuring the mass of the sample while the sample is in the sample receiving space, said means for determining the water content of the sample being adapted to utilize the mass of the sample in determining the relative water content of the sample.

7. The apparatus according to claim 1, wherein the volume of the sample receiving space is 0.5-5 $dm^3$.

8. An NMR-based method for measuring the water content of a sample of solids and/or slurries, the method comprising:

producing a homogeneous main magnetic field using a resistive electromagnet, subjecting the sample to said main magnetic field in order to produce a net magnetization to the sample, producing a magnetic RF pulse by means for producing a magnetic RF pulse for exciting a measurable RF magnetization to a sample at an operating frequency corresponding to the Larmor frequency of hydrogen nuclei in the sample, the operating frequency being directly proportional to said main magnetic field, and producing the RF magnetic field and the main magnetic field perpendicular to each other, measuring the RF signal of a free induction decay produced by the excited sample, and determining the water content in the sample on the basis of said measured RF signal, wherein by measuring the RF signal of the excited sample after a predetermined dead time after the excitation pulse, determining the water content of the sample by extrapolating the RF signal value to the time at the excitation pulse based on the measured RF signal and determining the water content of the sample on the basis of said extrapolated signal, using a sample space having a volume of at least 0.5 $dm^3$ inside the means for producing a magnetic RF pulse, and producing said main magnetic field by the cooled resistive electromagnet wound with an aluminum conductor an operating frequency of which is 400-2000 kHz.

9. The method according to claim 8, wherein the sample is a biomass sample.

10. The method according to claim 8, wherein the sample is in a solid or slurry form.

11. The method according to claim 8, wherein by using a passively cooled electromagnet and an operating frequency of 400-950 kHz.

12. The method according to claim 8, wherein by using an actively cooled electromagnet and an operating frequency of 950-2000 kHz.

13. The method according to claim 8, wherein by measuring the mass of the sample while the sample is in the sample receiving space and determining the water content of the sample based on the mass of the sample.

* * * * *